United States Patent
Ekman et al.

(10) Patent No.: US 10,080,882 B2
(45) Date of Patent: Sep. 25, 2018

(54) VALVED CONTAINER ASSEMBLY

(71) Applicant: CONSORT MEDICAL PLC, Hemel Hempstead (GB)

(72) Inventors: Matt Ekman, Macclesfield (GB); Ian Anderson, Burwell (GB)

(73) Assignee: CONSORT MEDICAL PLC, Hemel Hempstead (GB)

( * ) Notice: Subject to any disclaimer, the term of this patent is extended or adjusted under 35 U.S.C. 154(b) by 546 days.

(21) Appl. No.: 14/405,271

(22) PCT Filed: Jun. 14, 2013

(86) PCT No.: PCT/GB2013/051557
§ 371 (c)(1),
(2) Date: Dec. 3, 2014

(87) PCT Pub. No.: WO2013/186568
PCT Pub. Date: Dec. 19, 2013

(65) Prior Publication Data
US 2015/0144127 A1  May 28, 2015

(30) Foreign Application Priority Data
Jun. 15, 2012 (GB) .................... 1210654.8

(51) Int. Cl.
*A61M 11/00*   (2006.01)
*A61M 39/24*   (2006.01)
(Continued)

(52) U.S. Cl.
CPC .......... *A61M 39/24* (2013.01); *A61M 11/007* (2014.02); *A61M 11/065* (2014.02);
(Continued)

(58) Field of Classification Search
CPC .. A61M 39/24; A61M 11/065; A61M 11/007; A61M 15/08; A61M 15/0028;
(Continued)

(56) References Cited

U.S. PATENT DOCUMENTS 5,069,670 A * 12/1991 Vetter ..................... A61M 5/28
                                                    604/218
5,716,338 A *  2/1998 Hjertman ............ A61M 5/2448
                                                    604/191
(Continued)

FOREIGN PATENT DOCUMENTS

DE    10137962 A1    2/2003
EP     0191508 A1    8/1986
(Continued)

OTHER PUBLICATIONS

Japanese Office Action for Application No. JP20150516687, 3 pages.
(Continued)

*Primary Examiner* — Steven Douglas
(74) *Attorney, Agent, or Firm* — Taft Stettinius & Hollister LLP; Derek B. Lavender

(57) ABSTRACT

A valved container assembly (10) comprising a container (12) for containing a fluid, the container (12) extending in an axial direction and having at least one venting opening (12*a*) at a front end and at least one dispensing opening (12*b*). The valved container assembly (10) further comprising a valve (14) disposed in the container (12) and a plunger element (20) disposed axially rearward of the valve (14), the plunger element (20) being axially moveable in the container (12) and defining a first volume (22) in the container (12) between the plunger element (20) and the valve (14), where the plunger element (20) is configured to increase the pressure of a fluid in the first volume (22) upon axial movement relative to the valve (14). The valve (14) com-
(Continued)

prises a permanent seal (16) forming a fluidic seal between the at least one venting opening (12a) and the first volume (22), and a resilient seal (18) that is axially rearward of said permanent seal (16) and is moveable between a sealing configuration and an open configuration. In the sealing configuration the resilient seal (18) forms a fluidic seal with the container (12) between the at least one dispensing opening (12b) and the first volume (22). In at least one axial position of the valve (14) in the container (12) when the resilient seal (18) is in the open configuration the first volume (22) is fluidly connected to the at least one dispensing opening (12b). The resilient seal (18) is moveable from the sealing configuration to the open configuration upon fluid pressure in the first volume (22) exceeding a predetermined pressure threshold.

23 Claims, 2 Drawing Sheets

(51) Int. Cl.
*A61M 15/00* (2006.01)
*B05B 11/00* (2006.01)
*B05B 11/02* (2006.01)
*B65D 83/00* (2006.01)
*A61M 15/08* (2006.01)
*A61M 11/06* (2006.01)
*B05C 17/005* (2006.01)
*A61M 5/24* (2006.01)

(52) U.S. Cl.
CPC ........ *A61M 15/0028* (2013.01); *A61M 15/08* (2013.01); *B05B 11/007* (2013.01); *B05B 11/0054* (2013.01); *B05B 11/02* (2013.01); *B65D 83/0005* (2013.01); *A61M 5/2459* (2013.01); *A61M 2039/242* (2013.01); *A61M 2205/8225* (2013.01); *A61M 2205/8231* (2013.01); *A61M 2207/00* (2013.01); *A61M 2210/0618* (2013.01); *B05C 17/00593* (2013.01); *Y10T 29/4984* (2015.01)

(58) Field of Classification Search
CPC ........ A61M 2039/242; A61M 2207/00; A61M 2205/8231; B05B 11/007; B05B 11/02; B05B 11/0054; B65D 83/005; Y10T 29/4984
See application file for complete search history.

(56) References Cited

U.S. PATENT DOCUMENTS

| | | | |
|---|---|---|---|
| 7,503,907 B1* | 3/2009 | Lesch, Jr. | A61M 5/284 604/232 |
| 2005/0051162 A1* | 3/2005 | Schuler | B65D 83/54 128/200.23 |
| 2006/0149211 A1* | 7/2006 | Simpson | A61M 5/16804 604/403 |
| 2013/0228136 A1* | 9/2013 | Lyon | A01K 13/003 119/601 |
| 2015/0045747 A1* | 2/2015 | Anderson | A61M 15/0028 604/247 |

FOREIGN PATENT DOCUMENTS

| | | | |
|---|---|---|---|
| FR | 2130838 | | 11/1972 |
| FR | 2750051 | * | 6/1996 |
| JP | 2003275306 A | | 9/2003 |
| JP | 2008-502901 A | | 1/2006 |
| JP | 2006-516328 A | | 6/2006 |
| JP | 2008-544266 A | | 12/2008 |
| JP | 2009-162656 A | | 7/2009 |
| WO | WO2013/124670 A1 | | 8/2013 |

OTHER PUBLICATIONS

UK Search Report of Priority Application No. GB1210654.8 dated Sep. 25, 2012.
International Search Report and Written Opinion for PCT/GB2013/051557 dated Oct. 31, 2013.
International Preliminary Report on Patentability and Written Opinion for PCT/GB2013/051557 dated Dec. 16, 2014.

* cited by examiner

VALVED CONTAINER ASSEMBLY

This application is a U.S. national stage application under 35 U.S.C. § 371 of PCT International Application Serial No. PCT/GB2013/051557, which has an international filing date of Jun. 14, 2013 designates the United States of America, and claims the benefit of GB Application No. 1210654.8, which was filed on Jun. 15, 2012. The disclosures of each of these prior applications are hereby expressly incorporated by reference in their entirety.

This invention relates to a valved container assembly, and in particular to a valved container assembly having a self-opening valve.

BACKGROUND

GB2400040 (Bespak plc) describes a closure member for a container, such as a vial, that seeks to facilitate the delivery of a metered dose of medicament, for example, in a nasal dispenser. In particular, GB2400040 describes a container or vial for a fluid, the container comprising a casing defining an interior for storage of the fluid and a closure member. The closure member comprises a body and at least one resilient projection to seal in a storage condition an outlet of the casing, wherein upon an increase in the pressure of the interior of the container the at least one resilient projection is deflected to accommodate outflow of fluid through the outlet. In one described embodiment, the closure member has a sealing portion that seals the closure member to the container about the circumference of the closure member, and pressure in the interior of the container is increased by displacing the closure member into the container. In another described embodiment, the container is part of a dispensing apparatus. In this embodiment, however, the sealing portion is separate to the closure member and forms a bung that is displaceable in the interior of the container to increase the pressure therein.

It is an object of the present invention to provide an alternative valved container assembly for dispensing a fluid.

BRIEF SUMMARY OF THE DISCLOSURE

In accordance with a first aspect of the present invention there is provided a valved container assembly comprising:
  a container for containing a fluid, the container extending in an axial direction and having at least one venting opening at a front end and at least one dispensing opening;
  a valve disposed in the container; and
  a plunger element disposed axially rearward of the valve, the plunger element being axially moveable in the container and defining a first volume in the container between the plunger element and the valve, where the plunger element is configured to increase the pressure of a fluid in the first volume upon axial movement relative to the valve;
  where the valve comprises:
    a permanent seal forming a fluidic seal between the at least one venting opening and the first volume; and
    a resilient seal that is axially rearward of said permanent seal and is moveable between a sealing configuration and an open configuration;
  wherein in the sealing configuration the resilient seal forms a fluidic seal with the container between the at least one dispensing opening and the first volume;
  in at least one axial position of the valve in the container when the resilient seal is in the open configuration the first volume is fluidly connected to the at least one dispensing opening; and
  wherein the resilient seal is moveable from the sealing configuration to the open configuration upon fluid pressure in the first volume exceeding a predetermined pressure threshold.

The at least one axial position of the valve in the container in which the first volume is fluidly connected to the at least one dispensing opening when the resilient seal is in the open configuration may include the forwardmost axial position of the valve in the container.

The resilient seal may comprise one or more flexible elements, wherein the one or more flexible elements may partly extend circumferentially around said valve and the remainder of the valve forms a seal with the container circumferentially around said one or more flexible elements. Alternatively, the one or more flexible elements may extend entirely circumferentially around said valve.

The resilient seal may comprise at least two flexible elements, wherein the at least two flexible elements may be axially aligned with one another.

The permanent seal may comprise at least one flange projecting outwardly from said valve about the entire perimeter of the valve, said at least one flange sealing against said container. The permanent seal may comprise at least two flanges projecting outwardly from said valve about the entire perimeter of the valve, wherein the at least two flanges are arranged in axial alignment with one another.

The plunger element may comprise a plunger stopper.

The valve may comprise elastomeric material.

The valved container may be a primary pack for use as part of a dispensing apparatus.

The valved container assembly may be sized and configured for insertion into a human nasal cavity.

In accordance with a second aspect of the present invention, there is provided a dispensing apparatus including:
  a valved container assembly according to the first aspect of the present invention; and
  a power source for moving the plunger element of the valved container assembly so as to expel fluid from the first volume through the at least one dispensing opening.

The said valved container assembly may sized and configured for insertion into a human nasal cavity.

The power source may include a fluidic propellant that boils to create a gas pressure for moving the plunger element.

The fluidic propellant may include or consist of a hydrofluoroalkane (HFA).

The valved container may be releasably attachable to the remainder of the dispensing apparatus, wherein the releasable coupling may be a bayonet fitting. Said bayonet fitting may be between the valved container assembly and a housing of the dispensing apparatus.

In accordance with a third aspect of the present invention, there is provided a kit comprising a dispensing apparatus according to the second aspect of the present invention, and a plurality of further valved container assemblies, where each of the plurality of further valved container assemblies is individually releasably attachable to the remainder of the dispensing apparatus.

In accordance with a fourth aspect of the present invention, there is provided a method of assembling a valved container assembly, comprising the steps of:

providing a container that extends in an axial direction and has at least one venting opening at a front end and at least one dispensing opening that is axially rearwards of the venting opening;

inserting a valve in the container, where the valve comprises a permanent seal and a resilient seal that is axially rearward of the permanent seal;

axially moving the valve towards the front end of the container and allowing air between the front end of the container and the valve to exit the container through the venting opening;

filling the container axially rearward of the valve with a fluid;

inserting a plunger element axially rearward of the fluid so that the fluid is disposed between the valve and the plunger element. The fluid may be a medicament.

BRIEF DESCRIPTION OF THE DRAWINGS

Embodiments of the invention are further described hereinafter with reference to the accompanying drawings, in which:

FIG. 1A shows the valved container assembly prior to actuation, FIG. 1B shows the valved container assembly during delivery, and FIG. 1C shows the valved container assembly after delivery.

DETAILED DESCRIPTION

Figure 1A:
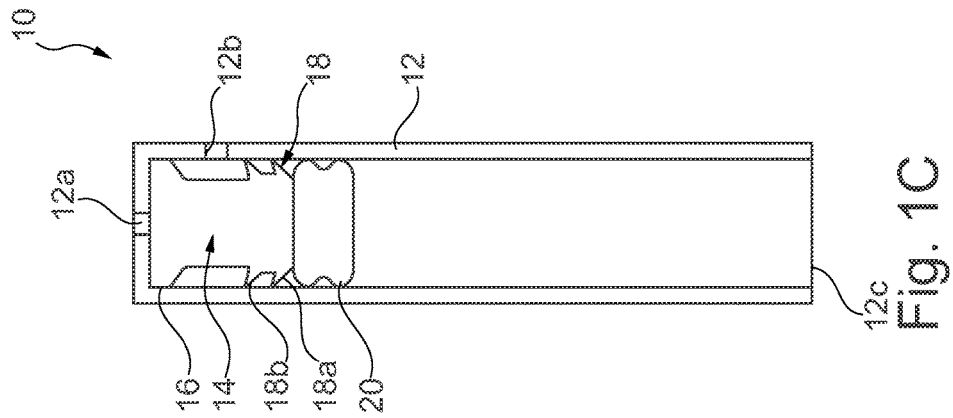
FIGS. 1A to 1C are a cross-sectional view showing a valved container assembly according to an embodiment of the present invention, in various stages of its operation, where
Figure 1B:
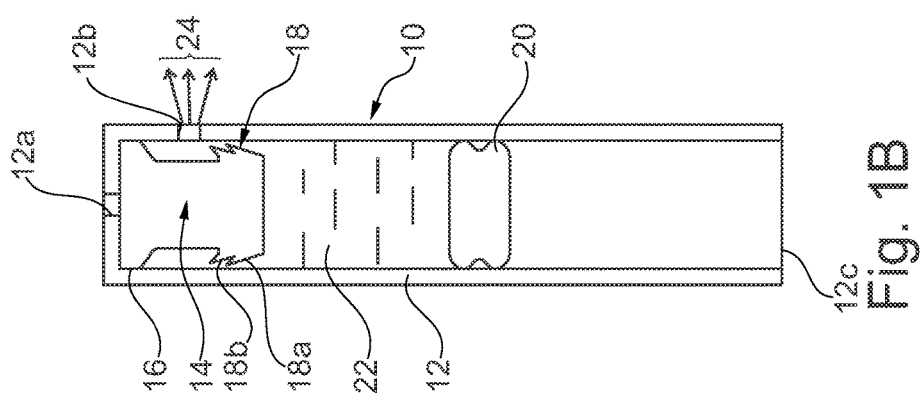
Figure 1C:
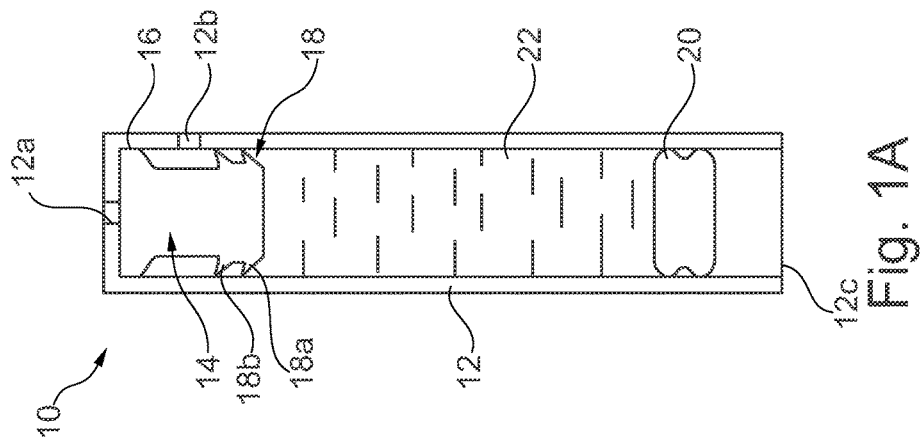

FIGS. 1A to 1C show the various stages of operation of a valved container assembly 10 in accordance with one embodiment of the present invention. The valved container assembly 10 could by any suitable container assembly for containing and dispensing a metered dose of a fluid such as a medicament, including but not limited to a syringe, vial or nasal spray. The valved container assembly 10 comprises a container 12 that preferably has a circular or rounded cross section (e.g. cylindrical or conical), a valve 14 disposed in the container 12 and a plunger element 20 disposed in the container 12. The container 12 extends along a longitudinal axis between a front end and a rear end. The container 12 has a venting opening 12a in the front end and has a rear opening 12c at the rear end. Additionally, the container 12 has a dispensing opening 12b intermediate the venting opening 12a and the rear opening 12c, which is axially rearward of the venting opening 12a. In the embodiment shown in the Figures, the dispensing opening 12b is a radial hole in the container 12. Indeed, where the dispensing opening 12b is axially rearward of the venting opening 12a, the dispensing opening 12b will be extend in a radial direction or at least have a radial component along its extension. Although the embodiment depicted in the Figures includes a single venting opening 12a and a single dispensing opening 12b, in alternative embodiments, there may be more than one venting opening 12a and/or more than one dispensing opening 12b. The one or more venting opening 12a and/or one or more dispensing opening 12b may take any suitable form such as, for example, a hole, slot or nozzle.

Throughout this application, references to "forward" or "front" or the like are in reference to the front end of the container 12 where the venting opening 12a is disposed. References to "axial" or the like are considered to denote directions parallel to the longitudinal axis of the container 12. References to "rearward" or "rear" or the like are in reference to the direction opposite the "forward" direction along an axial path.

The valve 14 is disposed in the container 12 at or near the front end of the container 12 and includes a permanent seal 16 that forms a fluid tight seal with the interior of the container around the periphery of the valve 14. In a preferable embodiment, the valve 14 is formed from an elastomeric material so that the sealing effect provided by the permanent seal 16 between the valve 14 and the container 12 is realized due to the elastomeric nature of the valve 14, and hence permanent seal 16.

Axially rearward of the permanent seal 16, the valve 14 has a resilient seal 18 that is formed of a pair of axially aligned flexible elements 18a,18b that extend radially from the valve 14 and extend around the entire periphery of the valve 14. The width (i.e. radial extent) of the valve 14 between the permanent seal 16 and the resilient seal 18 is less than the width of the permanent seal 16 so that the portion of the valve 14 between the permanent seal 16 and the resilient seal 18 does not contact the container 12. This formation results in an annulus formed between the valve 14 and the container 12 between the permanent seal 16 and the resilient seal 18. Whilst in the embodiment shown in the Figures has two flexible elements 18a, 18b, in alternative embodiments, the resilient seal 18 may include a single flexible element or three flexible elements, or more.

In alternative embodiments, the resilient seal 18 does not extend around the entire periphery (circumference) of the valve 14, where a further permanent seal seals the valve 14 to the container 12 in areas that the resilient seal 18 does not extend. In these alternative embodiments, an axial channel, rather than an annulus is formed between the valve and the container 12 axially between the permanent seal 16 and the resilient seal 18.

As is described in more detail below, the resilient seal 18 is moveable between a sealing configuration (as shown in FIG. 1A) and an open configuration (as shown in FIG. 1B), where in the sealing configuration, the resilient seal 18 fluidly seals the valve 14 to the container 12, and in the open configuration, the resilient seal 18 does not fluidly seal the valve 14 to the container 12.

Between the valve 14 and the plunger element 20 is defined a first volume 22 that can contain a fluid such as a fluidic medicament.

In a particularly preferable embodiment, the dispensing opening 12b is distanced axially rearward of the venting opening 12a by an amount that is less than the axial distance between the permanent seal 16 and the resilient seal 18, and more than the axial thickness of the permanent seal 16. In this preferable embodiment, when the valve 14 is disposed in its forwardmost axial position in the container 12, the permanent seal 16 seals the venting opening 12a and the dispensing opening 12b is axially disposed between the permanent seal 16 and the resilient seal 18.

When the resilient seal 18 is in the sealing configuration, it provides a fluidic seal with the container 12 between the first volume 22 and the dispensing opening 12b so as to prevent any fluid in the first volume 22 from exiting the container 12 through the dispensing opening 12b.

When the resilient seal 18 is in the open configuration, the first volume 22 is in fluid communication with the atmosphere via the dispensing opening 12b, subject to the axial position of the valve 14 in the container 12. Indeed, for the first volume 22 to be fluidly connected to the dispensing opening 12*b*, the dispensing opening 12*b* must be in fluid communication with the annuls (i.e. be axially aligned therewith) formed between the permanent seal 16 and the resilient seal 18 of the valve 14. In the case where a channel rather than an annulus is formed between the permanent seal 16 and the resilient seal 18, the dispensing opening 12*b* must be rotationally aligned and axially aligned with the channel for fluid communication to be established between the channel and the dispensing opening 12*b*.

In the preferable embodiment where the dispensing opening 12*b* is axially disposed between the permanent seal 16 and the resilient seal 18 when the valve 14 is disposed in its forwardmost axial position in the container 12, the first volume 22 will be fluidly connected to the dispensing opening 12*b* when the valve 14 is in its forwardmost axial position in the container 12 and the resilient seal 18 is in its open configuration. In the case where a channel rather than an annulus is formed between the permanent seal 16 and the resilient seal 18, restriction elements or other suitable means may be present to ensure that the valve 14 is correctly rotationally oriented so that the channel is in fluid communication with the dispensing opening 12*b*.

The resilient seal 18 is moved from the sealing configuration to the open configuration when a force incident on the resilient seal 18 exceeds at predetermined threshold. Such a force will arise when the fluid pressure of a fluid acting on the resilient seal 18 exceeds a predetermined threshold. For example, if the first volume 22 was filled with a fluid (such as a fluidic medicament), then the resilient seal 18 would move from the sealing configuration to the open configuration when the pressure of the fluid exceeded the predetermined threshold. When the pressure exceeds the predetermined threshold, the flexible elements 18*a*,18*b* of the resilient seal 18 flex or deflect so as to move away from the container 12 and open a fluid pathway allowing fluid to bypass the resilient seal 18. Alternative components may form the resilient seal 18 in place of the flexible elements 18*a*, 18*b* that deform, deflect, flex or otherwise move to open a fluid pathway between the valve 14 and the container 12 upon application of a predetermined force. In the embodiment shown in FIG. 1B, the flexible elements 18*a*,18*b* are shown to be flexed or deflected in a forward direction, such as one might expect to result from the pressure of a fluid in the first volume 22 exceeding the predetermined pressure threshold.

In both sealing and open configurations of the resilient seal 18, the permanent seal 16 remains in place and maintains a seal between the valve 14 and the container 12 axially forwards of the resilient seal 18. Therefore, the venting opening 12*a* is always fluidly sealed from the first volume 22.

FIG. 1A shows the valved container assembly 10 prior to actuation. The first volume 22 contains a fluid and the resilient seal 18 is in its sealing configuration. To actuate the device to dispense the fluid from the container 12, an axially forward force is applied to the plunger element 20 to increase the pressure of the fluid above the predetermined threshold. The axially forward force may be applied directly by a user (e.g. via a plunger rod), or the user may actuate a power source that then exerts or causes another element to apply an axially forward force on the plunger element 20.

In the embodiment shown in FIG. 1A, the valve 14 is already in its forwardmost axial position in the container 12, so the front end of the container 12 prevents any further axially forward movement of the valve 14 relative to the container 12. Therefore, the valve 14 remains axially stationary as it is acted upon by the force applied to the plunger element 20 due to the incompressible nature of fluid. The resilient seal 18 is therefore acted upon by the fluid, which is above the predetermined threshold, and the resilient seal 18 moves from the sealing configuration to the open configuration.

When in the open configuration, further axially forward movement of the plunger element 20 relative to the fixed valve 14 causes the fluid to flow from the first volume out through the dispensing opening 12*b* as depicted by arrows 24 in FIG. 1B.

Continued axially forward movement of the plunger element 20 relative to the fixed valve 14 causes all of the fluid in the first volume 22 to be expelled through the dispensing opening 12*b*, and the first volume 22 is reduced to substantially zero, as shown in FIG. 1C. At this point, the dispensing operation is complete.

The plunger element 20 may be accessed through the open rear end 12*c* of the container 12 and may additionally include a plunger rod or the like to facilitate its axial movement within the container 12. In a preferable embodiment, however, the plunger element 20 is acted upon by a gas pressure, for example provided by a propellant that boils to provide a suitable gas pressure for moving the plunger element 20. Amongst other possibilities within the scope of the present invention, suitable propellants include or entirely consist of hydrofluoroalkanes (HFA). The present invention is particularly suitable for the delivery of viscous drugs.

The container assembly 10 may be a primary pack that is used as part of a dispensing apparatus that additionally includes a power source for automatically moving the plunger element 20 to dispense a fluid. In a particularly preferable embodiment, the container 12 is shaped and configured for insertion into a human nasal cavity for delivery of a metered dose of medicament therein. In alternative embodiment, the container assembly may be configured for dispensing a metered dose of medicament to other areas of the body, which may or not be a cavity.

In an alternative or further preferable embodiment, several valved container assemblies 10 are provided for use as part of a reusable dispensing apparatus, of which the valved container assemblies 10 are the only disposable component. In this arrangement, the valved container assemblies 10 are each individually releasably attachable to the remainder of the dispensing apparatus, so that when one the medicament from one valved container assembly 10 has been dispensed, that valved container assembly 10 can be removed from the dispensing apparatus and replaced with another valved container assembly 10 for dispensing a further dose of medicament.

Figure 2:
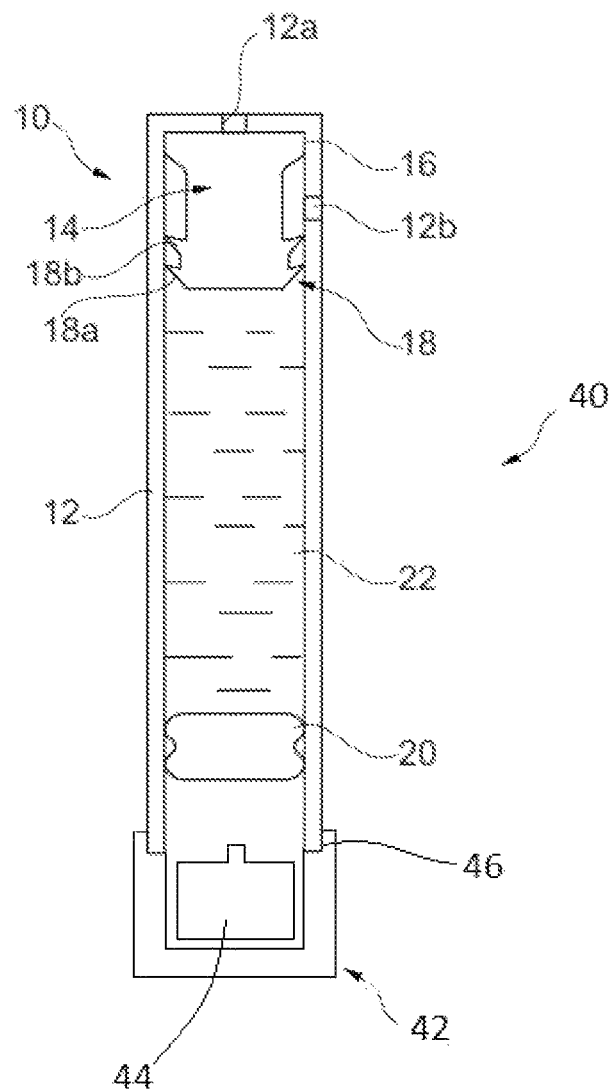
FIG. 2 shows a cross-sectional view of a dispensing apparatus in accordance with an embodiment of the present invention.

FIG. 2 shows a dispensing apparatus 40 in accordance with an embodiment of the present invention. The valved container assembly 10 is releasably connected to a housing 42 (which forms a remainder of the dispensing apparatus 40) by a releasable coupling 46.

The valved container assemblies 10 may be releasably attachable to the remainder of the dispensing apparatus by a bayonet fitting or other suitable mechanism that permits a secure fit but a user friendly removal and replacement. Other suitable connections include, but are not limited to, a screw fit, push fit or snap fit arrangement.

The valved container assemblies 10 may be provided in a pack that may have individually sealed compartments (e.g. a blister pack) for containing individual valved container assemblies 10 separately from one another.

In one embodiment, the valved container assemblies 10 may be supplied with or connected to an applicator, where the user grasps the applicator to connect the valved container assembly 10 to the remainder of the dispensing apparatus and then removes the applicator leaving the valved container assembly 10 attached to the remainder of the dispensing apparatus. The valved container assembly 10 may attach to the dispensing apparatus by any suitable connection mechanism, including but not limited to a bayonet fitting, a screw fit arrangement, a snap fit arrangement or a push fit arrangement.

The dispensing apparatus can include a canister or other suitable supply of propellant as a power source (labelled 44 in FIG. 2) for moving the plunger element 20 to dispense a dose of fluid from the container 12. The canister or other suitable supply of propellant may contain enough propellant to power a single dispensing action (i.e. the fluid from a single valved container assembly 10), or it may contain enough propellant to power a plurality of dispensing actions (i.e. the fluid from more than one valved container assemblies 10).

In accordance with an aspect of the present invention, a method of filling the valved container that includes the initial step of inserting the valve 14 in the container 12 with the permanent seal 16 entering the rear opening 12c of the container 12 first so that the permanent seal 16 is axially forwards of the resilient seal 18 in the container 12. Next, the valve 14 is axially moved towards the front end of the container 12. This action is permitted since air trapped between the valve 14 and the front end of the container 12 can exit the container 12 through the venting opening 12a. With the valve 14 at its forwardmost axial position, a fluid, such as fluidic medicament, can be introduced into the container 12 axially rearward of the valve 14. Once the fluid has been introduced, the plunger element 20 may be inserted into the container 12 axially rearward of the fluid so that the fluid is disposed between the valve 14 and the plunger element 20 (i.e. in the first volume 22). Such a method of assembly relies on the presence of the venting opening 12a to permit the translation of the valve 14 in the container 12 to its forwardmost axial position therein.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents, which are filed concurrently with or previous to this specification in connection with this application and which are open to public inspection with this specification, and the contents of all such papers and documents are incorporated herein by reference.

The invention claimed is:

1. A valved container assembly comprising:
   a container for containing a fluid, the container extending in an axial direction and having at least one venting opening at a front end and at least one dispensing opening;
   a valve disposed in the container; and
   a plunger element disposed axially rearward of the valve, the plunger element being axially moveable in the container and defining a first volume in the container between the plunger element and the valve, where the plunger element is configured to increase the pressure of a fluid in the first volume upon axial movement relative to the valve;
   where the valve comprises:
   a permanent seal forming a fluidic seal with the container around the periphery of the valve between the at least one venting opening and the first volume to fluidly seal the venting opening from the first volume; and
   a resilient seal that is axially rearward of said permanent seal and is moveable between a sealing configuration and an open configuration;
   wherein in the sealing configuration the resilient seal forms a fluidic seal with the container between the at least one dispensing opening and the first volume;
   in at least one axial position of the valve in the container when the resilient seal is in the open configuration the first volume is fluidly connected to the at least one dispensing opening; and
   wherein the resilient seal is moveable from the sealing configuration to the open configuration upon fluid pressure in the first volume exceeding a predetermined pressure threshold,
   further wherein, the permanent seal continues to form a fluidic seal between the at least one venting opening and the first volume when pressure in the first volume exceeds the predetermined threshold.

2. A valved container assembly according to claim 1, wherein the at least one axial position of the valve in the container in which the first volume is fluidly connected to the at least one dispensing opening when the resilient seal is in the open configuration includes the forwardmost axial position of the valve in the container.

3. A valved container assembly according to claim 1, wherein the resilient seal comprises one or more flexible elements.

4. A valved container assembly according to claim 3, wherein said one or more flexible elements partly extends circumferentially around said valve and the remainder of the valve forms a seal with the container circumferentially around said one or more flexible elements.

5. A valved container assembly according to claim 3, wherein said one or more flexible elements extends entirely circumferentially around said valve.

6. A valved container assembly according to 3, wherein the resilient seal comprises at least two flexible elements.

7. A valved container assembly according to claim 6, wherein the at least two flexible elements are axially aligned with one another.

8. A valved container assembly according to claim 1, wherein the permanent seal comprises at least one flange projecting outwardly from said valve about the entire perimeter of the valve, said at least one flange sealing against said container.

9. A valved container assembly according to claim 8, wherein the permanent seal comprises at least two flanges projecting outwardly from said valve about the entire perimeter of the valve, wherein the at least two flanges are arranged in axial alignment with one another.

10. A valved container assembly according to claim 1, wherein the plunger element comprises a plunger stopper.

11. A valved container assembly according to claim 1, wherein said valve comprises elastomeric material.

12. A valved container assembly according to claim 1, wherein the valved container is a primary pack for use as part of a dispensing apparatus.

13. A valved container assembly according to claim 1, wherein the assembly is sized and configured for insertion into a human nasal cavity.

14. A dispensing apparatus including:
    a valved container assembly according to claim 1; and
    a power source for moving the plunger element of the valved container assembly so as to expel fluid from the first volume through the at least one dispensing opening.

15. A dispensing apparatus according to claim 14, wherein said valved container assembly is sized and configured for insertion into a human nasal cavity.

16. A dispensing apparatus according to claim 14, wherein said power source includes a fluidic propellant that boils to create a gas pressure for moving the plunger element.

17. A dispensing apparatus according to claim 16, wherein said fluidic propellant includes a hydrofluoroalkane (HFA).

18. A dispensing apparatus according to claim 14, comprising a releasable coupling, wherein the valved container is releasably attachable to the remainder of the dispensing apparatus by attachment of the releasable coupling.

19. A dispensing apparatus according to claim 18, wherein said releasable coupling is a bayonet fitting.

20. A dispensing apparatus according to claim 19, wherein said bayonet fitting is between the valved container assembly and a housing of the dispensing apparatus.

21. A kit comprising a dispensing apparatus according to claim 18, and a plurality of further valved container assemblies, where each of the plurality of further valved container assemblies is individually releasably attachable to the remainder of the dispensing apparatus.

22. A method of assembling a valved container assembly, comprising the steps of:
    providing a container that extends in an axial direction and has at least one venting opening at a front end and at least one dispensing opening that is a radial hole in the container spaced axially rearwards of the at least one venting opening;
    inserting a valve in the container, where the valve comprises a permanent seal and a resilient seal that is axially rearward of the permanent seal;
    axially moving the valve towards the front end of the container and allowing air between the front end of the container and the valve to exit the container through the at least one venting opening;
    filling a first volume of the container axially rearward of the valve with a fluid, the permanent seal forming a fluidic seal with the container around the periphery of the valve between the at least one venting opening and the first volume to fluidly seal the at least one venting opening from the first volume; and
    inserting a plunger element axially rearward of the fluid so that the fluid is disposed between the valve and the plunger element.

23. A method according to claim 22, wherein the fluid is a medicament.

* * * * *